United States Patent
Boyt

(10) Patent No.: US 8,778,420 B1
(45) Date of Patent: Jul. 15, 2014

(54) TOPICAL SKIN CARE COMPOSITIONS

(71) Applicant: Gary Boyt, Amsterdam, NY (US)

(72) Inventor: Gary Boyt, Amsterdam, NY (US)

(\*) Notice: Subject to any disclaimer, the term of this patent is extended or adjusted under 35 U.S.C. 154(b) by 0 days.

(21) Appl. No.: 13/776,901

(22) Filed: Feb. 26, 2013

(51) Int. Cl.
*A61K 36/82* (2006.01)

(52) U.S. Cl.
USPC .......... 424/729; 424/727; 424/764; 424/401; 424/778

(58) Field of Classification Search
CPC .......... A61K 8/97; A61K 36/82; A61K 36/53
USPC .......................... 424/729, 727, 764, 401, 778
See application file for complete search history.

(56) References Cited

PUBLICATIONS https://web.archive.org/web/20110207152355/http://botanicalpotions.com—2011.*
Botanical Potions "Home" Page (http//www.botanicalpotions.com/#!) (Dec. 30, 2012) (last accessed Feb. 26, 2013).
Botanical Potions "About" Page (http//www.botanicalpotions.com/#!about) (Dec. 30, 2012) (last accessed Feb. 26, 2013).
Botanical Potions "Ingredients" Page (http//www.botanicalpotions.com/#!ingredients) (Dec. 30, 2012) (last accessed Feb. 26, 2013).
Botanical Potions "Testimonials" Page (http//www.botanicalpotions.com/#!testimonials) (Dec. 30, 2012) (last accessed Feb. 26, 2013).
Botanical Potions "Buy-Now" Page (http//www.botanicalpotions.com/#!buy-now) (Dec. 30, 2012) (last accessed Feb. 26, 2013).

\* cited by examiner

*Primary Examiner* — Susan Hoffman
(74) *Attorney, Agent, or Firm* — Fox Rothschild LLP; Gerard P. Norton

(57) ABSTRACT

This invention relates to compositions and applications for a topical skin care composition that includes from about 52 wt % to about 90 wt % *Camellia sinensis* (green tea) extract; from about 0.5 wt % to about 15 wt % *Calendula officinalis* extract; from about 0.5 wt % to about 10 wt % *Trifolium pratense* (red clover blossom) extract; from about 0.1 wt % to about 5 wt % *Lavandula angustifolia* essential oil in coco-caprylate/caprate; from about 0.5 wt % to about 5 wt % glycerin; an emulsifier component in an amount from about 2 wt % to about 10 wt %; and a preservative component in an amount from about 0.5 wt % to about 3 wt %, wherein the amounts are by total weight of the composition.

18 Claims, No Drawings

TOPICAL SKIN CARE COMPOSITIONS

BACKGROUND

Many options exist to improve the appearance and quality of skin. Therapeutic and cosmetic skin formulations aimed at replenishing skin moisture; protecting against on-going loss of moisture; removing dead skin cells; decreasing irritation; minimizing irritant release; and minimizing skin conditions associated with, for example, inflammation are among the most sought after formulations. However, such compositions often include harsh ingredients that can lead to unwanted side effects when applied to the skin. For example, petroleum jelly is inexpensive, abundant, and can be smoothly applied to the skin. However, petroleum jelly has a number of disadvantages. In particular, petroleum jelly is a petroleum based product which may cause contact dermatitis on the skin and can be toxic.

Therefore, a need exists for mild, "natural" topical skin care compositions that reduce the undesired toxicities associated with harsh chemicals while providing superior improvements to skin appearance and quality.

SUMMARY

There is provided in accordance with various embodiments a topical skin care composition that includes from about 52 wt % to about 90 wt % *Camellia sinensis* (green tea) extract; from about 0.5 wt % to about 15 wt % *Calendula officinalis* extract; from about 0.5 wt % to about 10 wt % *Trifolium pratense* (red clover blossom) extract; from about 0.1 wt % to about 5 wt % *Lavandula angustifolia* essential oil in coco-caprylate/caprate; from about 0.1 wt % to about 5 wt % glycerin; an emulsifier component in an amount from about 2 wt % to about 10 wt %; and a preservative component in an amount from about 0.5 wt % to about 3 wt %, wherein the amounts are by total weight of the composition.

In one embodiment, the emulsifier component includes a non-ionic emulsifier, an anionic emulsifier, a cationic emulsifier, or a combination thereof. In another embodiment, the emulsifier component includes a non-ionic emulsifier and a cationic emulsifier. In a further embodiment, the non-ionic emulsifier is cetearyl alcohol.

In one embodiment, the cationic emulsifier is behentrimonium methosulfate. In another embodiment, the preservative component includes gluconolactone and sodium benzoate.

In one embodiment, the *Camellia sinensis* (green tea) extract is present in an amount of about 82 wt %. In another embodiment, the *Calendula officinalis* extract is present in an amount of about 7.5 wt %. In a further embodiment, the *Trifolium pratense* (red clover blossom) extract is present in an amount of about 2.5 wt %. In yet another embodiment, the *Lavandula angustifolia* essential oil in coco-caprylate/caprate is present in an amount of about 0.5 wt %. In an additional embodiment, the glycerin is present in an amount of about 1 wt %. In another embodiment, the emulsifier component is present in an amount of about 5 wt %. In a further embodiment, the preservative component is present in an amount of about 1.5 wt %.

In one embodiment, the composition is in the form of a lotion or a cream.

Also presented is a method of treating a skin condition by topically applying to skin in need thereof a composition according to the present invention, wherein topical application of the composition to skin in need thereof ameliorates a skin condition. In one embodiment, the skin condition is selected from dry skin, itchy skin, inflamed skin, erythema, sensitive skin, pruritus, blotches, fine lines or wrinkles, sun damaged skin, dermatitis, psoriasis, folliculitis, rosacea, acne, eczema, sun burns, burned skin, and skin-inflammatory skin conditions. In another embodiment, the dermatitis condition is selected from seborrheic dermatitis, nummular dermatitis, contact dermatitis, atopic dermatitis, exfoliative dermatitis, perioral dermatitis, and stasis dermatitis.

Also provided is a kit that includes the composition of the present invention disposed within a container.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Pharmaceutically elegant" describes a composition that has particular tactile properties which feel pleasant on the skin (e.g., compositions that are not too watery or greasy, compositions that have a silky texture, compositions that are non-tacky or sticky, etc.). Pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The compositions of the present invention can comprise, consist essentially of, or consist of the claimed ingredients. The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In one aspect, compositions consisting essentially of the claimed ingredients excludes ingredients that would materially affect a given composition's ability to ameliorate a skin condition by, for example, but not limited to, moisturizing skin, healing damaged skin, softening calluses, softening skin, reducing wrinkles, healing chapped skin, and/or reducing or preventing dry skin or flaky skin. In another aspect, compositions consisting essentially of dermatologically acceptable vehicles excludes ingredients that would result in undue toxicity, incompatibility, instability, allergic response, and the like, when applied to skin.

As used in this document, the singular forms "a," "an," and "the" include plural references unless the context clearly dictates otherwise. Unless defined otherwise, all technical and scientific terms used herein have the same meanings as commonly understood by one of ordinary skill in the art.

DETAILED DESCRIPTION

The present inventor discovered a synergism of botanical extracts that when used in combination provides superior improvements in skin appearance and quality. Furthermore, the present compositions possess a stable shelf life (e.g. about 12-24 months un-opened) using mild, natural ingredients. Additionally, the compositions provide a soothing, aromatherapeutic scent without the need for synthetic fragrance chemicals.

Accordingly, this document describes a topical skin care composition that includes from about 52 wt % to about 90 wt % *Camellia sinensis* (green tea) extract; from about 0.5 wt % to about 15 wt % *Calendula officinalis* extract; from about 0.5 wt % to about 10 wt % *Trifolium pratense* (red clover blossom) extract; from about 0.1 wt % to about 5 wt % *Lavandula angustifolia* essential oil in coco-caprylate/caprate; from about 0.1 wt % to about 5 wt % glycerin; an emulsifier component in an amount from about 2 wt % to about 10 wt %; and a preservative component in an amount from about 0.5 wt % to about 3 wt %, wherein the amounts are by total weight of the composition.

In another embodiment, the amount of *Camellia sinensis* (green tea) extract ranges from about 57 wt % to about 85 wt %. In one embodiment, the *Camellia sinensis* (green tea) extract is present in an amount of about 82 wt %. In another embodiment, the *Calendula officinalis* extract is present in an amount of about 7.5 wt %. In an additional embodiment, the *Trifolium pratense* (red clover blossom) extract is present in an amount of about 2.5 wt %. In a further embodiment, the *Lavandula angustifolia* essential oil in coco-caprylate/caprate is present in an amount of about 0.5 wt %.

The compositions can be formulated as emulsions (e.g., oil-in-water, water-in-oil, water-in-oil-in-water, oil-in-water, oil-in-water-in-oil, etc.), creams, lotions, solutions (e.g., aqueous or hydro-alcoholic solutions), gels, ointments, milks, pastes, etc. The compositions can also be formulated for topical skin application at least 1, 2, 3, 4, 5, 6, 7, or more times a day during use.

In one embodiment, the *Camellia sinensis* (green tea) extract is incorporated into the composition of the present invention as an aqueous extract (e.g. *Camellia sinensis* (green tea) in distilled water). In another embodiment, the *Calendula officinalis* extract is incorporated into the composition of the present invention as a medium polar solvent extract (e.g. *Calendula officinalis* in coco-caprylate/caprate). In yet another embodiment, the *Trifolium pratense* (red clover blossom) extract is incorporated into the composition as an aqueous alcohol extract (e.g. *Trifolium pratense* (red clover blossom) in 50/50 ethanol/distilled water). However, most, if not all, of the alcohol in this component evaporates from the composition during processing.

In addition to the extraction processes described in the Examples, a person of ordinary skill in the art would be able to isolate any one of the extracts identified above from parts of the corresponding plant by using any suitable method known in the art. In one non-limiting example, the plant (or any part of the plant such as the leaves, stems, bark, roots, fruit, flowers or flower buds, seeds, seed pods, sap, whole plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at $-20°$ C. or lower, preferably under a vacuum for removal of water content (lyophilization). The resultant extract can then be used in the compositions of the present invention.

In other aspects, aqueous, alcoholic, or oil based extraction techniques, or combinations thereof, can be used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydrofluoro-carbon solvents), etc.

As noted above, the composition of the present invention includes an emulsifier component. In one embodiment, the emulsifier component includes a non-ionic emulsifier, an anionic emulsifier, a cationic emulsifier, or a combination thereof. In a further embodiment, the emulsifier component includes a non-ionic emulsifier and a cationic emulsifier. In an additional embodiment, the non-ionic emulsifier is cetearyl alcohol. In a further embodiment, the cationic emulsifier is behentrimonium methosulfate. In one embodiment, the emulsifier component is present in an amount of about 5 wt %.

The composition of the present invention also includes a preservative component. In one embodiment, the preservative component includes gluconolactone and sodium benzoate. In another embodiment, the preservative component is present in an amount of about 1.5 wt %.

The composition of the present invention also include glycerin. In a further embodiment, glycerin is present in an amount of about 1 wt %.

Also presented herein are methods of treating a skin condition by topically applying to skin in need thereof a composition of the present invention, wherein topical application of the composition to skin in need thereof treats or ameliorates the skin condition. The composition can be applied to a fine line or wrinkle, dry, flaky, or itchy skin, inflamed skin, and other skin associated disorders disclosed throughout this application. Non-limiting examples of skin conditions include dry skin, itchy skin, inflamed skin, erythema, sensitive skin, pruritus, blotches, fine lines or wrinkles, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, eczema, sun burns, burned skin, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein.

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a barrier container, a package, a compartment, or other types of containers such as injection or blow-molded plastic containers into which the compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a liquid, a fluid, or a semi-solid. The containers can have pump or squeeze mechanisms. A kit can also include instructions for using the kit and/or compositions. Instructions can include an explanation of how to apply, use, and maintain the compositions.

The following non-limiting examples serves to further illustrate the present invention.

EXAMPLES

Example 1

Preparation of Botanical Extracts

*Camellia sinensis* (green tea) leaf extract was prepared by combining 113 g *Camellia sinensis* with 3790 g distilled water. The combination was then heated to 65° C. for 30 minutes while covered. After heating, the precipitate was filtered.

*Calendula officinalis* extract was prepared by combining 227 g *Calendula officinalis* with 1814 g coco-caprylate/caprate. The combination was allowed to stand sealed for 30 days with intermittent shaking. After this period, the precipitate was filtered.

*Trifolium pratense* (red clover blossom) extract was prepared by combining 227 g *Trifolium pratense* with 1814 g aqueous ethanol solvent (50/50 ethanol-distilled water). The combination was allowed to stand sealed for 30 days with intermittent shaking. After this period, the precipitate was filtered.

*Lavandula angustifolia* essential oil in coco-caprylate/caprate was prepared by combining 907 g *Lavandula angustifolia* essential oil with 907 g coco-caprylate/caprate. The combination was allowed to stand sealed for 30 days with intermittent shaking to produce an oil-in-oil infusion. After this period, the precipitate was filtered.

Example 2

Preparation of Topical Skin Care Composition 3790 g *Camellia sinensis* leaf extract was combined with 52 g gluconolactone, 17 g sodium benzoate, and 46 g vegetable glycerin to form composition "A". 347 g *Calendula officinalis* extract was combined with 57 g behentrimonium methosulfate and 170 g cetearyl alcohol to form composition "B". 116 g *Trifolium pratense* blossom extract was combined with 22.7 g *Lavandula angustifolia* essential oil in coco-caprylate/caprate to form composition "C". Compositions A and B were separately heated to 77° C. for 20 minutes. Following this period, composition B was poured into composition A with high-shear mixing. This combination was then cooled to 49° C. with mixing. Composition C was added to the combination of A and B with mixing. The final composition was then bottled and cooled to room temperature.

Example 2

Composition Testing

The skin of a volunteer human subject's hands was contacted and compromised (e.g. skin became dry and/or cracking) with a strong base solution of distilled water, sodium laureth sulfate, ethanol and sodium carbonate. A composition prepared in accordance with Example 1 was applied to the compromised skin twice daily for four days. Visual results (e.g. placing hand under a microscope) were recorded and are presented below in Table 1. "Day 0" refers to skin quality prior to applying the composition of Example 1.

TABLE 1

Daily observations of skin quality.

| Day | Observations |
|---|---|
| 0 | Skin was stripped of natural oil and moisture. The surface was dull and rough with fine wrinkles and cracking. Scratching the surface caused white scaling and redness. |
| 1 | The lotion rubbed in nicely and had a very soothing effect. Itching stops almost immediately and the scaling disappeared. |
| 2 | Fine wrinkles have hydrated and the cracks are healing over. Redness is gone and the skin feels smooth. |
| 3 | Cracks are barely visible to the naked eye. Skin looks and feels very smooth. |
| 4 | No visual signs of dry skin. Skin looks and feels healthy. |

Example 3

Additional Assays that can be Used to Test Compositions

The efficacy of compositions of the present invention can also be determined by methods known to those of ordinary skill in the art. The following are non-limiting assays that can be used in the context of the present invention. It should be recognized that other testing procedures can be used, including, for example, objective and subjective procedures.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region Immediately after reading, the area is treated with a composition of the present invention. Repeat measurements are taken at regular intervals to determine the formula's ability to reduce redness, inflammation, or skin irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations are made independently by two clinicians and averaged.

Skin Smoothness and Wrinkle Reduction Assay With Methods Disclosed in Packman and Gams, J. Soc. Cos. Chem., 29:70-90 (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skids surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A topical skin care composition comprising from about 52 wt % to about 90 wt % *Camellia sinensis* (green tea) extract; from about 0.5 wt % to about 15 wt % *Calendula officinalis* extract; from about 0.5 wt % to about 10 wt % *Trifolium pratense* (red clover blossom) extract; from about 0.1 wt % to about 5 wt % *Lavandula angustifolia* essential oil in coco-caprylate/caprate; from about 0.1 wt % to about 5 wt % glycerin; an emulsifier component in an amount from about 2 wt % to about 10 wt %; and a preservative component in an amount from about 0.5 wt % to about 3 wt %, wherein the amounts are by total weight of the composition.

2. The composition of claim 1, wherein the emulsifier component comprises a non-ionic emulsifier, an anionic emulsifier, a cationic emulsifier, or a combination thereof.

3. The composition of claim 2, wherein the emulsifier component comprises a non-ionic emulsifier and a cationic emulsifier.

4. The composition of claim 3, wherein the non-ionic emulsifier is cetearyl alcohol.

5. The composition of claim 3, wherein the cationic emulsifier is behentrimonium methosulfate.

6. The composition of claim 1, wherein the preservative component comprises gluconolactone and sodium benzoate.

7. The composition of claim 1, wherein the *Camellia sinensis* (green tea) extract is present in an amount of about 82 wt %.

8. The composition of claim 1, wherein the *Calendula officinalis* extract is present in an amount of about 7.5 wt %.

9. The composition of claim 1, wherein the *Trifolium pratense* (red clover blossom) extract is present in an amount of about 2.5 wt %.

10. The composition of claim 1, wherein the *Lavandula angustifolia* essential oil in coco-caprylate/caprate is present in an amount of about 0.5 wt %.

11. The composition of claim 1, wherein the glycerin is present in an amount of about 1 wt %.

12. The composition of claim 1, wherein the emulsifier component is present in an amount of about 5 wt %.

13. The composition of claim 1, wherein the preservative component is present in an amount of about 1.5 wt %.

14. The composition of claim 1, wherein the composition is in the form of a lotion or a cream.

15. A method of treating a skin condition comprising topically applying to skin in need thereof the composition of claim 1, wherein topical application of the composition to skin in need thereof ameliorates a skin condition.

16. The method of claim 15, wherein the skin condition is selected from the group consisting of dry skin, itchy skin, inflamed skin, erythema, sensitive skin, pruritus, blotches, fine lines or wrinkles, sun damaged skin, dermatitis, psoriasis, folliculitis, rosacea, acne, eczema, sun burns, burned skin, and skin-inflammatory skin conditions.

17. The method of claim 16, wherein the dermatitis condition is selected from the group consisting of seborrheic dermatitis, nummular dermatitis, contact dermatitis, atopic dermatitis, exfoliative dermatitis, perioral dermatitis, and stasis dermatitis.

18. A kit comprising the composition of claim 1 disposed within a container.

* * * * *